US00PP27028P3

(12) United States Plant Patent
Musacchi et al.

(10) Patent No.: US PP27,028 P3
(45) Date of Patent: Aug. 9, 2016

(54) PEAR TREE NAMED 'PE2UNIBO'

(50) Latin Name: ***Pyrus communis* L.**
Varietal Denomination: PE2UNIBO

(71) Applicant: Alma Mater Studiorum—Università di Bologna, Bologna (IT)

(72) Inventors: Stefano Musacchi, Wenatchee, WA (US); Vincenzo Ancarani, Bologna (IT); Silviero Sansavini, Bologna (IT)

(73) Assignee: Alma Mater Studiorum—Università di Bologna, Bologna (IT)

( * ) Notice: Subject to any disclaimer, the term of this patent is extended or adjusted under 35 U.S.C. 154(b) by 99 days.

(21) Appl. No.: 14/121,607

(22) Filed: Sep. 24, 2014

(65) Prior Publication Data

US 2015/0327417 P1 Nov. 12, 2015

(30) Foreign Application Priority Data

May 9, 2014 (QZ) ..... PBR 2014/0970

(51) Int. Cl.
*A01H 5/08* (2006.01)

(52) U.S. Cl.
USPC ..... Plt./176

(58) Field of Classification Search
USPC ..... Plt./176
See application file for complete search history.

(56) References Cited

PUBLICATIONS

PLUTO Plant Variety Database Feb. 19, 2016. p. 1.*

* cited by examiner

*Primary Examiner* — Annette Para
(74) *Attorney, Agent, or Firm* — Foley & Lardner LLP

(57) ABSTRACT

A new and distinct *Pyrus communis* L. pear tree variety named 'PE2UNIBO' is particularly characterized by the following features: medium vigorous trees with semi-upright growing habitus; bearing habitus normally on spurs on 2-3 years old branches and on 1 year shoots; good grafting compatibility with the main quince rootstocks; early ripening (about 15 days before 'Bartlett'); high and constant yield and early bearing; good size of the fruit (over 200 g) with regular pyriform shape; green skin at picking time and yellow-green at full ripening stage (after the cold storage), with an attractive red-orange over-color in the fruit surface previously exposed to sun; tender, juicy and white flash, with a very good flavor (good sugar-acid balance) at full ripening stage; long storage capacity in cold room, up to 5-6 months.

5 Drawing Sheets

Latin name of the genus and species of the plant claimed: *Pyrus communis* L.

Variety denomination: 'PE2UNIBO'.

CROSS-REFERENCE TO RELATED APPLICATIONS

This application claims priority to European Community Plant Variety Office Plant Breeders' Rights Application No. 2014/0970 filed May 9, 2014.

BACKGROUND OF THE INVENTION

The present invention relates to a new and distinct variety of pear tree, botanically known as *Pyrus communis* L. of the Rosaceae family, and hereinafter referred to by the variety denomination 'PE2UNIBO'.

The new *Pyrus* variety is a product of a controlled breeding program conducted by the inventors, Stefano Musacchi, Silviero Sansavini and Vincenzo Ancarani, in Cadriano (Bologna), Italy. The variety is fully owned by Alma Mater Studiorum—Università di Bologna. The objective of the breeding program was to develop a new *Pyrus* variety with high and constant yield, early ripening, high fruit quality and long storability in cold room.

The new *Pyrus* variety originated from a cross made by the inventors in 1992 in Cadriano (Bologna), Italy. The female or seed parent is the *Pyrus communis* L. variety designated 'Harvest Queen' (unpatented). The male or pollen parent is the *Pyrus communis* L. variety designated 'Abbé Fétel' (unpatented). The new *Pyrus* variety was discovered and selected by the inventors within the progeny of the stated cross in a controlled environment in 2001 in Cadriano (Bologna), Italy.

Asexual reproduction of the new *Pyrus* variety by budding and grafting was first performed in August 2001 in Cadriano (Bologna), Italy, and has demonstrated that the combination of characteristics as herein disclosed for the new variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'PE2UNIBO' which in combination distinguish this pear tree as a new and distinct variety:

1. Trees with medium vigor;
2. Early ripening;
3. Good graft compatibility with quince rootstocks;
4. High and constant yield;
5. High quality fruit with good flavor;
6. Large fruit size;

7. Green-yellow skin; and
8. Long storage capacity

In comparison to the parental varieties, 'Harvest Queen' and 'Abbé Fétel', the claimed variety differs primarily in the traits listed in Table 1.

TABLE 1

| Trait | New Variety 'PE2UNIBO' | Female Parent 'Harvest Queen' (unpatented) | Male Parent 'Abbé Fétel' (unpatented) |
|---|---|---|---|
| Compatibility with quince rootstock | Good | Partially | Partially |
| Fruit Shape | Pyriform; | Pyriform-truncated | Pyriform elongated |
| Fruit Size | Large | Small | Large |
| Skin color | Green-yellow | Yellow | Yellow |
| Taste | Sweet and sour | Sweet | Sweet |
| Harvest time | Early (15 days before 'Bartlett' pear) | Early (10 days before 'Bartlett' pear) | Late (30 days after 'Bartlett' pear) |

Of the many commercial varieties known to the present inventors, the most similar in comparison to the new *Pyrus* variety 'PE2UNIBO' is the *Pyrus* variety 'Bartlett' (unpatented), in the following characteristics described in Table 2:

TABLE 2

| Characteristic | New Variety 'PE2UNIBO' | Comparison Variety 'BARTLETT' |
|---|---|---|
| Growth habit | Semi-upright | Upright |
| Compatibility with quince rootstock | Compatible | Incompatible |
| Skin color | Green-yellow | Green-yellow |
| Fruit Shape | Pyriform; regular shape | Pyriform with maximum diameter slightly toward calyx; irregular shape |
| Size | Large | Medium |
| Harvest time | Early | Medium |

BRIEF DESCRIPTION OF THE DRAWINGS

The accompanying photographs illustrate the overall appearance of the new *Pyrus* variety 'PE2UNIBO' showing the colors as true as is reasonably possible with colored reproductions of this type. Colors in the photographs may differ slightly from the color values cited in the detailed botanical description, which accurately describe the color of 'PE2UNIBO'.

DETAILED BOTANICAL DESCRIPTION

Figure 1:
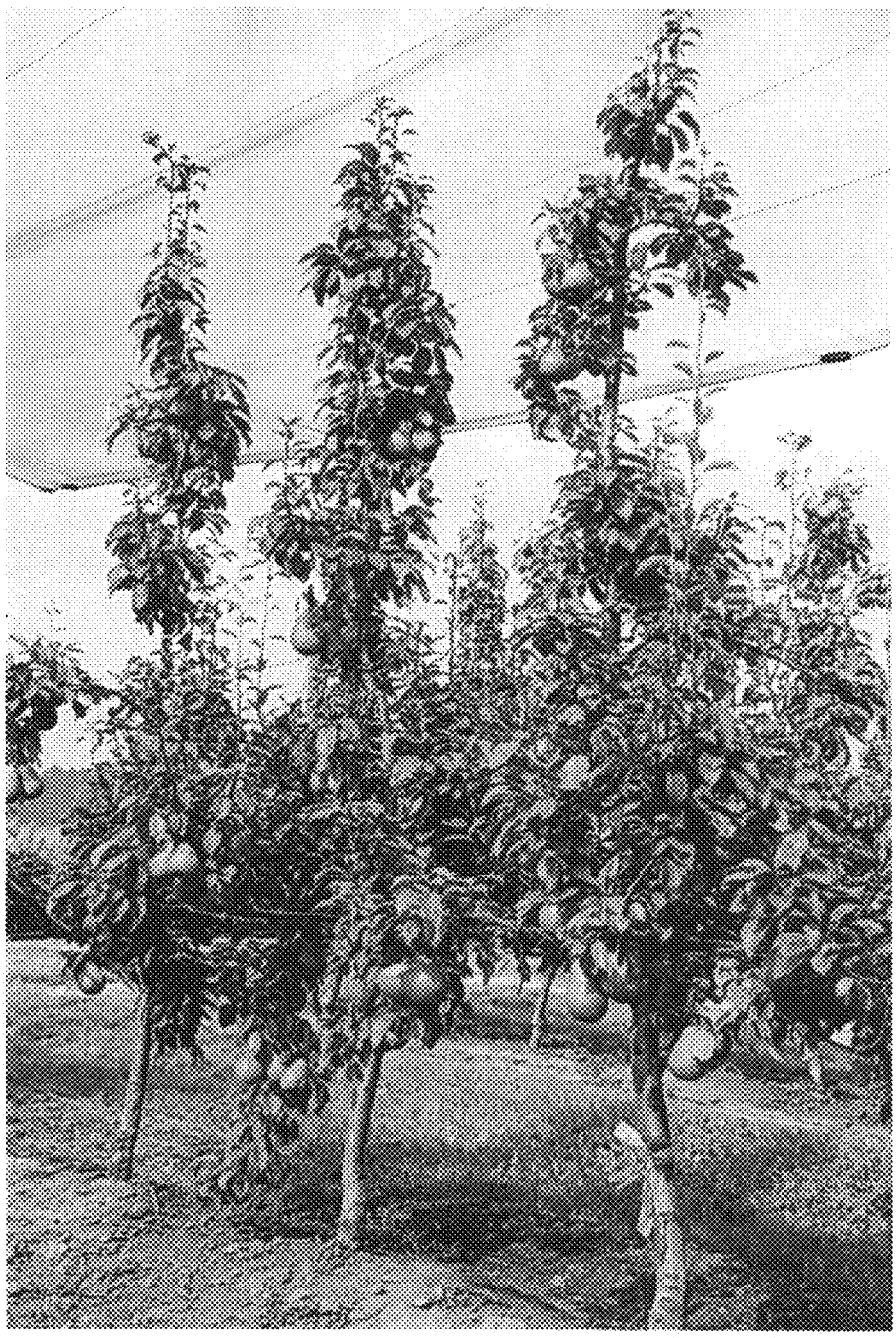
FIG. 1—shows a tree of 'PE2UNIBO', at six years old.
Figure 2:
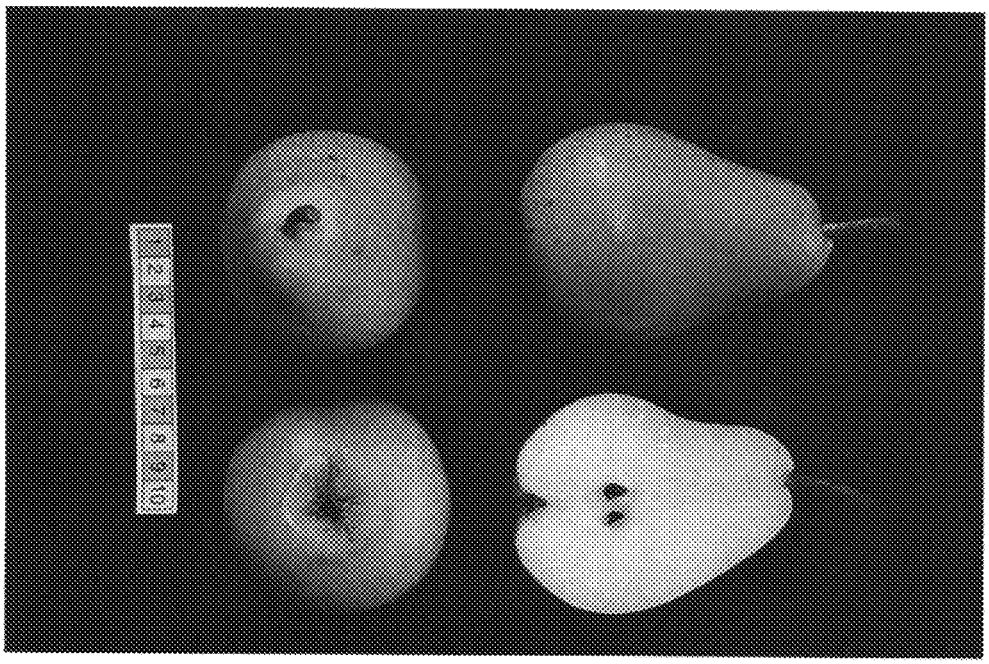
FIG. 2—shows typical fruits of 'PE2UNIBO'.
Figure 3:
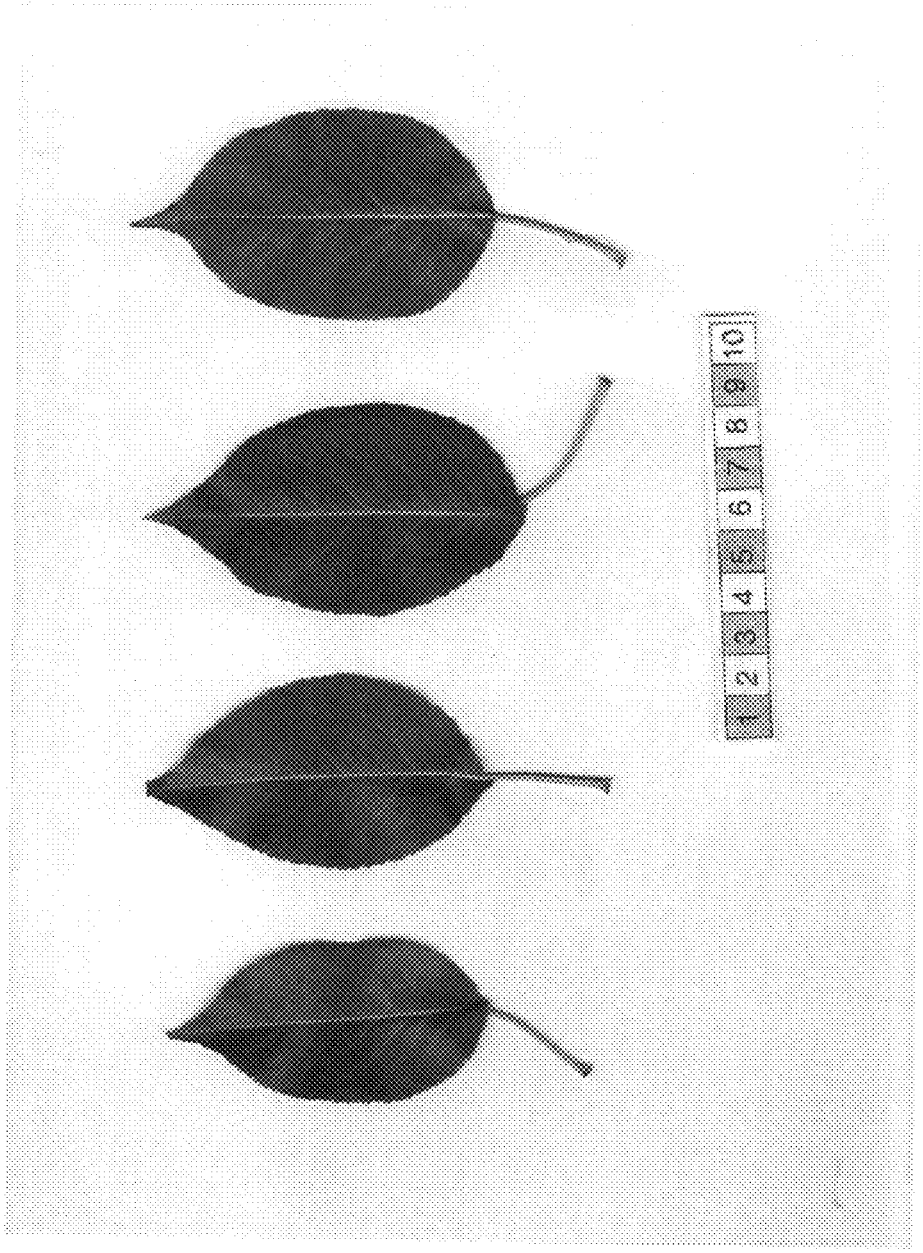
FIG. 3—shows the leaves of 'PE2UNIBO'.
Figure 4:
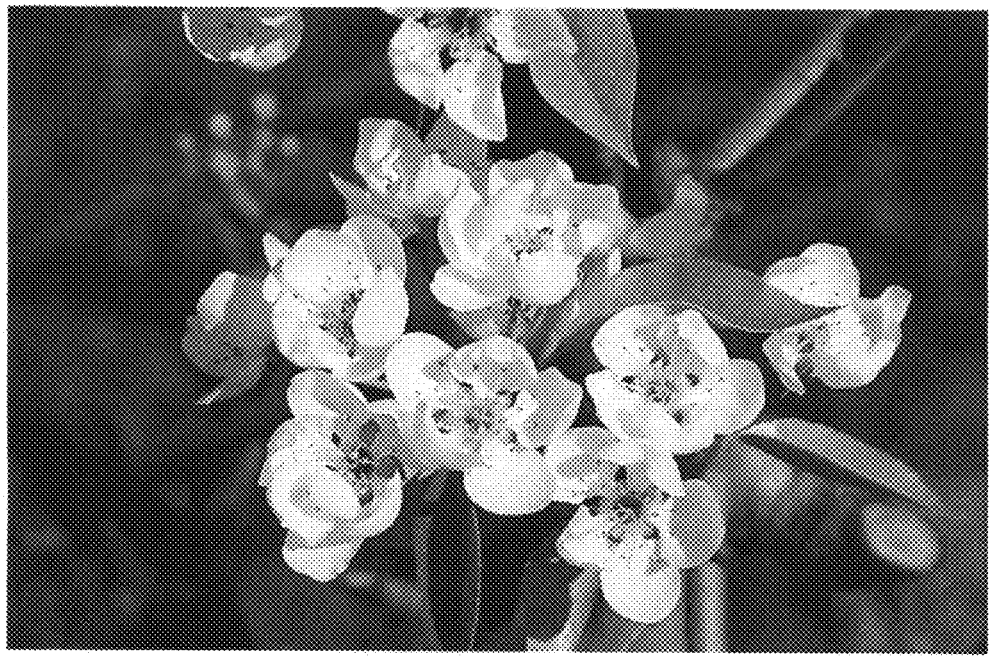
FIGS. 4 and 5—show different images of the flowers of 'PE2UNIBO', at full bloom.
Figure 5:
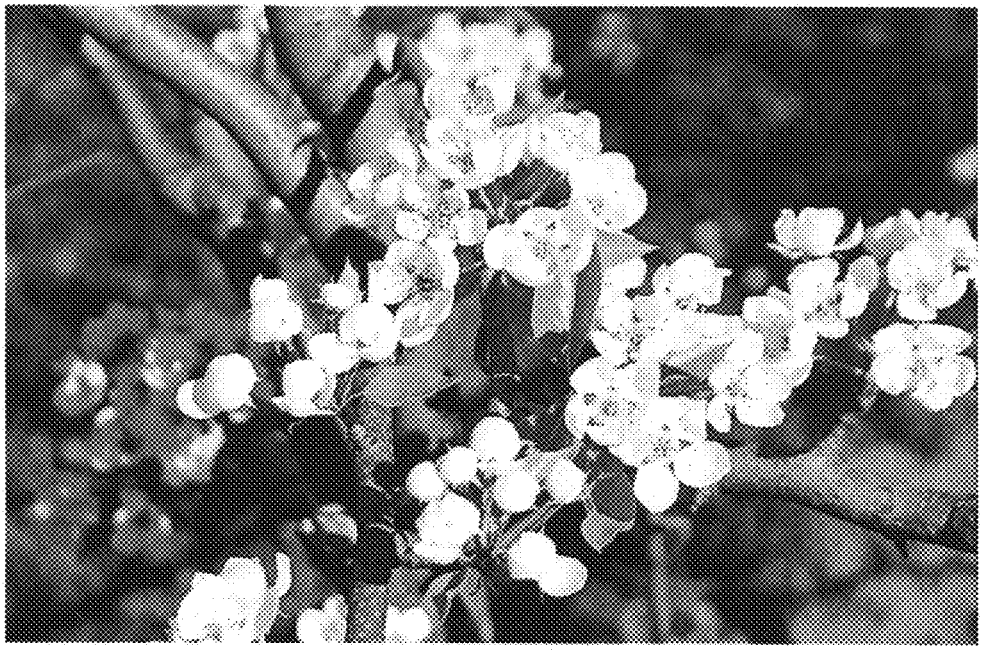

The new *Pyrus* variety 'PE2UNIBO' has not been observed under all possible environmental conditions. The phenotype of the new variety may vary with variations in environment such as temperature, light intensity, and day length without any change in the genotype of the pear tree.

The aforementioned photographs, together with the following observations, measurements and values describe trees of 'PE2UNIBO' as grown in the pear farm in Cadriano (Bologna), Italy, under conditions which closely approximate those generally used in commercial practice. The pear farm in which PE2UNIBO is growing has a clay soil; the climate is temperate continental with high summer temperatures and low winter temperatures; the orchard has a drip irrigation system used for fertigation Unless otherwise stated, the detailed botanical description includes observations, measurements and values based on six year old 'PE2UNIBO' trees grown in the pear farm in Cadriano (Bologna), Italy from 2009 to 2014. Quantified measurements are expressed as an average of measurements taken from a number of trees of 'PE2UNIBO'. The measurements of any individual tree, or any group of trees, of the new variety may vary from the stated average.

Color references are made to The Royal Horticultural Society Colour Chart (R.H.S.), except where general colors of ordinary significance are used. Color values were taken under daylight conditions at approximately at 10:00 am in Cadriano (Bologna), Italy.

All of the trees of 'PE2UNIBO', insofar as they have been observed, have been identical in all the characteristics described below.

Classification:

*Botanical.*—*Pyrus communis* L.

*Commercial.*—*Pyrus* cv. PE2UNIBO.

Parentage:

*Female or seed parent.*—*Pyrus* variety designated 'Harvest Queen' (unpatented).

*Male or pollen parent.*—*Pyrus* variety designated 'Abbé Fétel' (unpatented).

Propagation: Budding and grafting.

Growing conditions:

*Light intensities.*—Full sunlight.

*Temperature* (*in the vegetative season, from March to September, year* 2013).—Minimum: 0.1° C. in March. Maximum: 38.9° C. in August. Medium: 8° C. (March) to 26.3° C. (July).

*Fertilization.*—A balanced fertilizer with level of N 80 kg/ha; $P_2O_5$ 50 kg/ha; $K_2O$ 120 kg/ha.

*Growth regulators.*—Not used.

*Pruning or trimming requirements.*—Winter pruning.

Tree:

*Age.*—Observed trees were 6 years old and grafted on quince rootstock BA29®.

*Vigor.*—Medium vigor; early bearing; mid-season bloom, abundant flowering; high and constant productivity; no biennial bearing. The variety is compatible with the main quince and pear rootstocks.

*Type of bearing.*—Typically on spurs on 2-3 years old branches and on 1 year shoots.

*Form.*—Semi-upright and conical: branches inserted with a semi-narrow crotch angle. Forms also depends on the training system used.

*Habit.*—A medium sized tree with one trunk and one leader. The tree habitus is semi-upright with the main branches spreading laterally semi-upward; symmetrical crown and rounded shape.

*Branching habit.*—Main branches angle is 30° to 70° with respect to trunk if allowed to grow naturally. The crotch angle changes along the trunk: the basal branches have a more right crotch angle whereas the upper and apical branches have a more narrow crotch angle.

*Density.*—Medium-low density.

*Size at maturity* (*depends on the training system*).—Height: About 2.9 m. Spread: About 1.4 m.

*Trunk.*—Height (up to leaders): About 2.6 m. Diameter: About 55 mm (measured 10 cm above the grafter point).

*Texture.*—At first, it is smooth with numerous lenticels, then it shows shallow furrows and scaly ridges. Generally the lenticels are numerous, with irregular shape, from rounded to elongated and also arranged vertically to form a vertical lines of pustules.

*Bark color.*—Primarily RHS 197B, with RHS 175A under bark.

*Trunk lenticels.*—Length: About 3.5 mm. Width: About 1.3 mm. Color: RHS 199A. Density: 2.02 n°/cm$^2$.

*Branches.*—Number per tree: About 16 (from 10 to 19). Length: Varies due to pyramidal shape of tree; maximum of 80 cm to 90 cm; minimum of 15 cm to 50 cm. Diameter: About 11 mm to 27 mm. Surface texture: smooth with rounded and rough lenticels. Pubescence: Absent. Color: Mature (after about 3 years old): RHS 200C; under bark RHS 167A. New Growth: RHS 164A. Internode length (in the middle of branches): About 2.5 cm to 4 cm. Internode diameter (in the middle of branches): About 3.6 mm to 7 mm. Branch lenticels: Length: About 1.6 mm. Width: About 1.8 mm. Color: RHS 165B. Density: 3.8 n°/cm$^2$. One Year old Shoot lenticels (small and ovate): Length: About 0.34 mm to 1.19 mm. Width: About 0.35 mm to 0.87 mm. Color: RHS 164D. Density: 3.6 n°/cm$^2$.

*Spur.*—Present: Yes. Distance between each spur: On the 3 years old branches, the distance is about 3 mm to 7 mm. Diameter of each spur: About 5.6. Number of fruit per spur: About 2 to 4.

*Leaves.*—

*Arrangement.*—Alternate, simple, petiolated and arranged outwards in relation to shoot. Lamina Size: Length: About 6.94 mm (from 4.7 to 9.4 mm fully expanded leaf). Width: About 4.03 mm (from 2.5 to 5.8 mm fully expanded leaf). Length/width ratio: 1.7. Overall Shape: the shape of leaf blade is oval-elliptic with a medium pointed tip; the leaf area is medium: 21.4 cm$^2$; the longitudinal axis is slightly curved; Base shape: right-angled. Apex shape: slightly acute. Margin: bluntly serrate. Texture: Upper surface: glabrous. Under surface: glabrous. Pubescence: Upper surface: absent. Under surface: absent. Color (mature leaves): Upper surface: RHS 147A. Under surface: RHS 147C. Color (immature leaves): Upper surface: RHS 144A. Under surface: RHS 146D.

*Venation.*—Type: pinnate venation from central vein to the leaf edge. Color: RHS 151A.

*Petiole.*—Length: About 2.9 mm. Diameter: About 1.1 mm. Color: RHS 151A.

*Stipule.*—Arrangement: present in small numbers; the distance from basal attachment of petiole is short. Length (distance of stipules from basal attachment of petiole): About 1.5 mm to 11 mm. Width: About 4 mm to 13 mm.

Inflorescence:

*Blooming time.*—Full bloom on about April 2$^{nd}$, year 2012 in Cadriano (Bologna), Italy.

*Blooming period: About* 12 days, from March 28$^{th}$ to April 8$^{th}$.

*Fragrance.*—Not detected.

*Type.*—Corymb.

*Number of flowers per inflorescence.*—About 5 to 8.

*Inflorescence size.*—Diameter: About 8.5 cm. Depth: About 5 cm.

*Buds* (*vegetative bud on* 1 *year shoot*).—Terminal Buds: Number per spur: About 1-2. Shape: elongated and pointed. Length: About 8.9 mm. Width: About 4.2 mm. Color: Apex, RHS 200D, and base, RHS 200A. Texture: smooth; the bud support ranges from medium to big. Pubescence: Absent. Lateral Buds: Number per spur: About 1. Shape: elongated and pointed; acute apex; the position of vegetative bud in relation to shoot is slightly held out; the bud support has generally a medium size. Length: About 6.4 mm. Width: About 3.3 mm. Color: Apex, RHS 200C, and base, RHS 200B. Texture: smooth; medium bud support. Pubescence: Absent. Flower Buds (on 2-3 years old branches): Number per spur: 1 to 3. Shape: elongated and pointed. Length: About 8.1 mm. Width: About 3.4 mm. Color: Apex, RHS 166A, and base, RHS 200C. Texture: smooth. Pubescence: Absent.

*Petals.*—Number per flower: Five. Size: medium. Overall shape: the margins of petals touch each other. Apex shape: rounded. Base shape: rounded. Texture (upper surface): smooth. Texture (lower surface): smooth. Margin: entire. Color (upper surface): White at full bloom. Color (lower surface): White at full bloom.

*Sepals.*—Number per flower: Five.

*Pollination requirements.*—Can be pollinated by several varieties of pear trees.

Fruit:

*Keeping quality.*—The fruit keeps well on the tree; The fruit can be stored in cold temperature conditions for up to 5-6 months without loss of firmness and juiciness. The shelf life ranges from one week to ten days without having a loss of firmness and juiciness.

*Maturity when described.*—Ripe for eating.

*Maturity period after full bloom.*—About 115 days after full bloom on July 25$^{th}$.

*Type.*—Pome.

*General shape.*—Pyriform truncate, regular, with the maximum diameter slightly towards calyx; the fruit profile is straight to slightly concave. The stem is medium sized.

*Average weight.*—About 250 g.

*Fruit size.*—Average height: About 102 mm. Average diameter (at widest point): About 78 mm. Height/thickness ratio: 1.3.

*Stem.*—Length: About 32.6 mm. Diameter: About 4.0 mm. Color: RHS 165A.

*Basin.*—Depth: About 9.3 mm. Width: About 22.9 mm.

*Calyx.*—Depth: About 8.58 mm. Width: About 7.73 mm. Crowning at calyx end: weak. Calyx tube: Closed (it does not communicate with locules). At harvest, the sepals are converging or erect.

*Skin.*—Thickness: thin. Texture: smooth; with a red-orange over-color in the fruit exposed to sun. The over-color increases during storage. Color: RHS 144A (at picking time); RHS151D (when full ripe). Lenticels: very small and round, point shape; not measured. Color: RHS 199B. Density: 42.1 n°/cm$^2$.

*Flesh.*—Firmness (at picking time): 5.0 to 5.5 kg (measured with an 8 mm tip). Color: RHS 155A. Texture: tender and juicy at full ripening time. Aroma: rather aromatic, good Flavor. Sugar content (at picking time): 12.6° Brix. Acidity/Starch (at picking time) 3.8 g/lt malic acid. Core: Symmetry of core: symmetric.

Distinctness of core lines: medium. Locules: Number (per fruit): 5. Length: About 13 mm. Width: About 8 mm. Form: the seed almost fills the locule cavity.

Seeds:

*Number per fruit.*—About 1 to 10.

*Number per locule.*—About 1 to 2.

*Shape.*—Ovate.

*Length.*—About 8.2 mm.

*Width.*—About 4 mm.

*Texture.*—Smooth.

*Color.*—RHS 165A.

Use: Fresh market.

Disease/pest resistance: Unknown; test for tolerance to Fire Blight (*Erwinia amylovora*) in progress.

Disease/pest susceptibility: None observed.

Winter hardiness: No winter cold damage to wood and buds of dormant pear trees have been observed during the years of evaluation; but open flowers and young fruitlets are killed by exposure to −1.5 to −3° C., depending on the length of exposure.

Drought/heat tolerance: Tolerant to temperatures up to 38° C., growth is limited by drought periods without irrigation.

What is claimed is:

1. A new and distinct variety of *Pyrus communis* L. pear tree named 'PE2UNIBO', as illustrated and described herein.

* * * * *